United States Patent
Caputo et al.

(10) Patent No.: US 12,125,590 B2
(45) Date of Patent: *Oct. 22, 2024

(54) CONTROLLING PHYSICAL PROPERTY ACCESS USING HEALTH PARAMETERS

(71) Applicant: ShowingTime.com, Inc., Seattle, WA (US)

(72) Inventors: Michael P. Caputo, Aurora, IL (US); Scott E. Woodard, New Buffalo, MI (US)

(73) Assignee: MFTB Holdco, Inc., Seattle, WA (US)

( * ) Notice: Subject to any disclaimer, the term of this patent is extended or adjusted under 35 U.S.C. 154(b) by 294 days.

This patent is subject to a terminal disclaimer.

(21) Appl. No.: 17/890,151

(22) Filed: Aug. 17, 2022

(65) Prior Publication Data

US 2022/0392634 A1 Dec. 8, 2022

Related U.S. Application Data (63) Continuation-in-part of application No. 16/984,982, filed on Aug. 4, 2020, now Pat. No. 11,468,985.

(51) Int. Cl.
*G16H 40/67* (2018.01)
*A61B 5/11* (2006.01)
*A61B 5/145* (2006.01)

(52) U.S. Cl.
CPC ............ *G16H 40/67* (2018.01); *A61B 5/1118* (2013.01); *A61B 5/14532* (2013.01)

(58) Field of Classification Search
CPC .............................. G16H 40/67; G06Q 50/163
See application file for complete search history.

(56) References Cited

U.S. PATENT DOCUMENTS

| 5,014,049 A | 5/1991 | Bosley |
| 5,245,652 A | 9/1993 | Larson et al. |

(Continued)

FOREIGN PATENT DOCUMENTS

WO 2017174526 A1 10/2017

OTHER PUBLICATIONS

Ron Amadeo, "Huawei's Temperature-Taking Smartphone Is the Most 2020 Phone of 2020", Jun. 8, 2020, retrieved from https://arstechnica.com/gadgets/2020/06/huaweis-temperature-taking-smartphone-is-the-most-2020-phone-of-2020/ on Jul. 30, 2020, 6 pages.

(Continued)

*Primary Examiner* — Aryan E Weisenfeld
(74) *Attorney, Agent, or Firm* — VLP Law Group LLP; James A. D. White (57) ABSTRACT

A real estate showing appointment management system manages showing appointments based on a health parameter of a showing contact. The health parameter can be the body temperature. The system includes a server system running a server software application and software application running on a device. The software application configures the thermometer of the device to take body temperature of the showing contact. The thermometer can be an infrared thermometer. The software application determines whether the body temperature meets a threshold relying on the server system or by itself. When the showing contact passes the health check, the software application retrieves a showing directive for the showing contact to proceed with showing the listing of a showing appointment. The showing directive is presented by the device for the showing contact.

20 Claims, 9 Drawing Sheets

(56) References Cited

U.S. PATENT DOCUMENTS

| | | | |
|---|---|---|---|
| 5,280,518 A | 1/1994 | Danler et al. | |
| 5,475,375 A | 12/1995 | Barrett et al. | |
| 5,612,683 A | 3/1997 | Trempala et al. | |
| 5,705,991 A | 1/1998 | Kniffin et al. | |
| 5,974,406 A | 10/1999 | Bisdikian et al. | |
| 6,101,480 A | 8/2000 | Conmy et al. | |
| 6,157,315 A | 12/2000 | Kokubo et al. | |
| 6,300,873 B1 | 10/2001 | Kucharczyk et al. | |
| 6,385,541 B1 | 5/2002 | Blumberg | |
| 6,496,776 B1 | 12/2002 | Blumberg et al. | |
| 6,522,875 B1 | 2/2003 | Dowling et al. | |
| 6,594,633 B1 | 7/2003 | Broerman | |
| 6,624,742 B1 | 9/2003 | Romano et al. | |
| 6,636,803 B1 | 10/2003 | Hartz, Jr. et al. | |
| 6,727,801 B1 | 4/2004 | Gervasi et al. | |
| 6,842,105 B1 | 1/2005 | Henderson et al. | |
| 6,973,432 B1 | 12/2005 | Woodard et al. | |
| 7,009,489 B2 | 3/2006 | Fisher | |
| 7,058,395 B2 | 6/2006 | Dowling et al. | |
| 7,127,475 B2 | 10/2006 | Gotz et al. | |
| 7,191,058 B2 | 3/2007 | Laird et al. | |
| 7,193,503 B2 | 3/2007 | Fisher | |
| 7,292,844 B2 | 11/2007 | Dowling et al. | |
| 7,518,485 B2 | 4/2009 | Shuster | |
| 7,606,558 B2 | 10/2009 | Despain et al. | |
| 7,664,801 B2 | 2/2010 | Walker | |
| 7,728,711 B2 | 6/2010 | Shoenfeld | |
| 7,853,479 B2 | 12/2010 | Bengson | |
| 7,869,941 B2 | 1/2011 | Coughlin et al. | |
| 7,880,584 B2 | 2/2011 | Larson et al. | |
| 7,999,656 B2 | 8/2011 | Fisher | |
| 8,035,480 B2 | 10/2011 | Woodard et al. | |
| RE43,068 E | 1/2012 | Woodard et al. | |
| 8,145,352 B2 | 3/2012 | Woodard et al. | |
| 8,368,507 B2 | 2/2013 | Conreux et al. | |
| 8,385,897 B1 | 2/2013 | Yadav-Ranjan | |
| 8,451,088 B2 | 5/2013 | Fisher | |
| 8,649,486 B1 | 2/2014 | Kellogg et al. | |
| 8,754,744 B2 | 6/2014 | Woodard et al. | |
| 8,831,970 B2 | 9/2014 | Weik et al. | |
| 8,947,530 B1 | 2/2015 | Scalisi | |
| 8,971,506 B2 | 3/2015 | Kellogg et al. | |
| 9,194,157 B2 | 11/2015 | Bahar | |
| 9,208,466 B2 | 12/2015 | Fisher | |
| 9,311,656 B2 | 4/2016 | Barnes | |
| 9,460,480 B2 | 10/2016 | Woodard et al. | |
| 9,478,083 B2 | 10/2016 | Fisher | |
| 9,514,586 B2 | 12/2016 | Rogers et al. | |
| 9,536,359 B1 | 1/2017 | Gokcebay | |
| 9,659,334 B2 | 5/2017 | Fenn | |
| 9,659,424 B2 | 5/2017 | Huber et al. | |
| 9,761,071 B2 | 9/2017 | Woodard et al. | |
| 9,916,742 B2 | 3/2018 | Kuenze | |
| 9,978,192 B1 | 5/2018 | Nicosia et al. | |
| 9,990,787 B2 | 6/2018 | Capaldi-Tallon | |
| 10,026,248 B2 | 7/2018 | Woodard et al. | |
| 10,044,519 B2 | 8/2018 | Kasmir et al. | |
| 10,713,740 B1 | 7/2020 | Caputo | |
| 2002/0022980 A1 | 2/2002 | Mozayeny et al. | |
| 2002/0174090 A1 | 11/2002 | Dexter | |
| 2003/0038708 A1 | 2/2003 | Lund | |
| 2003/0154573 A1 | 8/2003 | Gould | |
| 2003/0179075 A1 | 9/2003 | Greenman | |
| 2005/0149432 A1 | 7/2005 | Galey | |
| 2005/0168320 A1 | 8/2005 | Henderson et al. | |
| 2005/0192930 A1 | 9/2005 | Hightower et al. | |
| 2005/0288958 A1 | 12/2005 | Eraker et al. | |
| 2006/0106628 A1 | 5/2006 | Faherty et al. | |
| 2006/0220809 A1 | 10/2006 | Stigall et al. | |
| 2007/0100644 A1 | 5/2007 | Keillor et al. | |
| 2007/0143173 A1 | 6/2007 | Walker et al. | |
| 2007/0266081 A1 | 11/2007 | Murchison et al. | |
| 2007/0290798 A1 | 12/2007 | Larson et al. | |
| 2008/0168369 A1 | 7/2008 | Tadman et al. | |
| 2008/0169937 A1 | 7/2008 | Lowry | |
| 2011/0053557 A1 | 3/2011 | Despain et al. | |
| 2012/0290203 A1 | 11/2012 | King | |
| 2013/0005368 A1 | 1/2013 | Hunziker | |
| 2013/0262186 A1 | 10/2013 | Lazarre et al. | |
| 2013/0282524 A1 | 10/2013 | Appolito et al. | |
| 2014/0258042 A1 | 9/2014 | Butler et al. | |
| 2014/0304178 A1 | 10/2014 | Bengson et al. | |
| 2015/0077220 A1 | 3/2015 | Davis et al. | |
| 2015/0081327 A1 | 3/2015 | Mooker | |
| 2015/0235145 A1 | 8/2015 | Dubuc | |
| 2016/0180620 A1 | 6/2016 | Eyring et al. | |
| 2016/0241999 A1 | 8/2016 | Chin et al. | |
| 2016/0275762 A1 | 9/2016 | Keunzi | |
| 2016/0364928 A1 | 12/2016 | Woodard et al. | |
| 2018/0075681 A1 | 3/2018 | Scalisi et al. | |
| 2018/0232978 A1 | 8/2018 | Schmidt-Lackner et al. | |
| 2019/0244455 A1 | 8/2019 | Kim et al. | |
| 2019/0327448 A1 | 10/2019 | Fu et al. | |

OTHER PUBLICATIONS

Mark Wilson, "Huawei's Clever New Smartphone Can Take Your Temperature", Jun. 8, 2020, retrieved from https://www.fastcompany.com/90513189/huaweis-new-smartphone-can-take-your-temperature on Jul. 30, 2020, 14 pages.

Jules Wang, "Huawei Announces a Phone That Can Take Your Temperature", Jun. 3, 2020, retrieved from https://androidpolice.com/2020/06/03/huawei-announces-a-phone-that-can-take-your-temperature/ on Jul. 30, 2020, 8 pages.

Alibaba Clouder, "Developing an Infrared Thermometer With an App Based on the WiFi Module of AliOS", Apr. 17, 2020, retrieved from https://www.alibabacloud.com/blog/developing-an-infrared-thermometer-with-an-app-based-on-the-wifi-module-of-alios_596131 on Jul. 30, 2020, 26 pages.

"The Hottest Thermometer. The Coolest Technology", retrieved from https://www.withings.com/us/en/thermo on Jul. 30, 2020, 23 pages.

Bluetooth Thermometers, retrieved from https://www.medicalexpo.com/medical-manufacturer/bluetooth-thermometer-44144.html on Jul. 30, 2020, 21 pages.

Rob Plowden et al., "How to Screen for the Coronavirus at Your Property Without Breaking the Law", Mar. 31, 2020, retrieved from https://www.globest.com/2020/03/31/how-to-screen-for-the-coronavirus-at-your-property-without-breaking-the-law/?slreturn=20220420114007 on May 20, 2022, 6 pages.

CONTROLLING PHYSICAL PROPERTY ACCESS USING HEALTH PARAMETERS

CROSS-REFERENCE TO RELATED APPLICATIONS

This application is a continuation-in-part of co-pending U.S. patent application Ser. No. 16/984,982, filed Aug. 4, 2020 and entitled "System And Method For Managing Property Showing Appointments Based On Health Parameters", which is hereby incorporated by reference in its entirety.

TECHNICAL FIELD OF THE DISCLOSURE

The present disclosure relates generally to automated techniques for controlling access of users to physical properties based at least in part on health parameters of the users, including performing automated activities involving assessing and using body temperature and/or other health parameters of the users.

DESCRIPTION OF BACKGROUND

Users participating in transactions involving real estate properties may perform various activities, such as managing information of various types (e.g., listings, listing agent profiles, showing agent profiles, showings of the listings, etc.), creating, scheduling, and managing showing appointments, communicating with others regarding real estate listings (e.g., to collect and forward showing feedback), etc. A showing appointment indicates a listing for a real estate property, the time or time period of the showing and the showing agent. A listing includes descriptions of the underlying real estate property, contact information of listing contacts (such as the listing agent, the listing office, the seller, etc.), showing instructions of the listing for showing agents, available showing time of the listing, etc. A showing agent may make showing appointments for showing real estate properties to their clients, such as prospect home buyers and tenants. As used herein, the showing agents, the prospect home buyers, the prospect tenants and other types of individuals on the showing side are referred to herein as showing contacts.

Various communications may occur between the listing contacts and the showing contacts, such as requests for showing feedback from showing agents, feedback received from showing agents and forwarded to listing agents, requests from showing agents to schedule showing appointments and confirmations from associated listing agents of the showing appointments, etc. Such users may perform such activities using mobile apps and software running on computer devices (e.g., desktop computers, laptop computers, tablet computers, etc.).

At the time of a particular showing appointment, the showing agent visits the listing and shows the underlying real estate property to her/his client. To do so, the showing agent may use a mobile app running on a mobile device (such as a smartphone), such as by communicating with a server system over the Internet. The mobile app may retrieve a showing pass, showing instructions and/or the listing access details from the showing appointment management system over the Internet.

However, showing real estate properties during a pandemic raises concerns for the listings' owners, residents and other related persons. For instance, a homeowner and/or the corresponding listing agent may desire to restrict or prohibit any person with a contagious virus to visit a property.

SUMMARY OF THE DISCLOSURE

Generally speaking, pursuant to various embodiments, the present disclosure provides automated techniques for controlling access of users to physical properties based at least in part on health parameters of the users, including performing automated activities involving assessing and using body temperature and/or other health parameters of the users. In at least some embodiments, some or all of the automated techniques are implemented by an improved real estate showing appointment management system, such as a system executing on one or more server computer devices and communicating with mobile electronic communication devices of users over the Internet and/or using other communication mediums, and/or executing on such mobile electronic communication devices, and with the real estate showing appointment management system including one or more specialized server software applications executing on the one or more server computer devices and/or one or more specialized mobile software applications executing on one or more of the mobile electronic communication devices. The system may, for example, limit or prevent showings of listings when a showing contact user exhibits a symptom of a virus or other infection or other indicated condition, including when a showing contact exhibits an abnormal body temperature or one or more other health parameters that satisfy one or more defined criteria. The system may, for example, include a database storing and providing real estate showing appointment data; a real estate showing appointment management server system having a server processing unit, a memory, and a network interface operatively coupled to the processing unit and operatively coupled to the database and the Internet; a specialized server software application running on the server processing unit; and a specialized software application running on an electronic communication device adapted to communicate with the real estate showing appointment management server system over the Internet. The specialized software application may, for example, be adapted to request one or more showing appointments from the specialized server software application over the Internet; receive the showing appointment(s) information from the specialized server software application over the Internet; present the showing appointment(s) on a display screen of the electronic communication device; in response to an input, select a showing appointment of the showing appointment(s), thereby forming a selected showing appointment; determine a first geographical location of a listing corresponding to the selected showing appointment; determine a second geographical location of the electronic communication device; determine whether the electronic communication device is within a geofence of the listing based on the geofence, the first geographical location and the second geographical location; and, when the electronic communication device has moved into the geofence, perform a health check process for determining whether one or more showing contact users will be allowed to proceed with the selected showing appointment. The health check process may, for example, include configuring or otherwise using the electronic communication device of a showing contact user to determine one or more values of one or more health parameters for the user (e.g., by using the electronic communication device to obtain such a health parameter value from one or more associated devices of the user, such as a smart watch, an electronic health tracker, an electronic activity tracker, a pacemaker or other implantable electronic heart device (e.g., implantable cardioverter-defibrillator), etc.; by using the electronic communication device to measure or estimate or otherwise predict such a health parameter value; by using the electronic communication device to obtain such a health parameter value from one or more other nearby devices that are now owned by or controlled by the user, such as a fixed-location infrared thermometer device or other thermometer device; etc.); and then determining whether the value(s) match one or more health thresholds or otherwise satisfy one or more defined criteria, such as with the determining performed by the electronic communication device or by one or more other computer devices (e.g., server computer devices) after retrieving the value(s) from the electronic communication device. A specialized mobile software application (e.g., the specialized server software application, the specialized software application on an electronic communication device of a showing contact user, etc.) may be further adapted to, when the value(s) match the health threshold(s) for one or some or all showing contact users, retrieve a showing directive for the selected showing appointment (e.g., from the specialized server software application) and present the showing directive via the electronic communication device(s) of one or some or all showing contact users (e.g., displayed on the display screen of an electronic communication device, presented in an audio format, etc.). In some embodiments and situations, the health parameter is a human body temperature parameter, the one or more values for a user are determined by a thermometer, and the one or more health thresholds includes a normal body temperature limit, such as with the one or more values matching one or more health thresholds when each value is below a normal body temperature limit or otherwise satisfies one or more defined criteria, and with the one or more values not matching the one or more health thresholds when any value is above the normal body temperature limit or otherwise does not satisfy one or more defined criteria. The showing directive may, for example, include at least one of a showing pass or a key code or other access code (e.g., for a listing physical access control device at the real estate property corresponding to the selected showing appointment), and may optionally further include showing instructions. In some embodiments and situations, the health check process includes obtaining one or more health parameter values by presenting one or more health inquiries to a showing contact user via the electronic communication device of the user (whether in addition to or instead of measuring body temperature or otherwise obtaining one or more other health parameter values) retrieving one or more responses to the one or more health inquiries via the electronic communication device, and determining whether the response(s) meet health requirements, such as by the electronic communication device and/or by one or more other computer devices (e.g., server computer devices). Furthermore, the present disclosure provides computer-implemented methods for controlling access of users to physical properties based at least in part on health parameters of the users in accordance with such described techniques, including performing automated activities involving assessing and using body temperature and/or other health parameters of the users.

In some embodiments and situations, the described techniques include implementing and/or using a real estate showing appointment management system comprising one or more processors; and one or more memories with stored software that, when executed by the one or more processors, causes the one or more processors to perform operations including at least: obtaining information about a showing appointment scheduled for a property during a time period, including multiple users that are scheduled to participate in the showing appointment and that each has a respective associated electronic communication device; establishing a geofence around the property before the time period; and controlling access of the multiple users to the property for the showing appointment, including, for each of the multiple users, determining that the electronic communication device associated with the user is within the geofence; performing, in response to the determining and before the showing appointment begins, a health check process for the user, including using the electronic communication device associated with the user to determine one or more values for one or more health parameters for the user, and determining whether the one or more values satisfy one or more defined criteria; and presenting, on the electronic communication device associated with the user, a showing directive to enable the showing appointment to occur only if the one or more values for the one or more health parameters for the user are determined to satisfy the one or more defined criteria. Such a real estate showing appointment management system may further involve one or more of the following: the showing directive including at least one of a showing pass or a key code corresponding to the showing appointment; and/or the performing of the health check process for a user including presenting a set of health inquiries to the user via the electronic communication device associated with the user, and determining whether a set of responses to the set of health inquiries obtained via the electronic communication device meets a set of health requirements; and/or the one or more processors and the one or memories being part of one or more server computer devices, with the operations include exchanging electronic communications between the one or more server computer devices and the electronic communication devices associated with the multiple users; and/or the real estate showing appointment management system further comprising the electronic communication devices that are associated with the multiple users and that include multiple processors and multiple memories, with the one or more processors including at least the multiple processors, and with the one or memories including at least the multiple memories; and/or the one or more health parameters including at least one (e.g., two or more of) of heart rate, or heart rate variability, or blood pressure, or respiratory rate, or walking pace, or distance traveled, or blood oxygen level, or blood glucose level, or calories expended, or sleep characteristics; and/or with the electronic communication device associated with one of the multiple users including at least one of a smart watch, or an electronic health tracker, or an electronic activity tracker, or a pacemaker, or an implantable electronic heart device; and/or with the electronic communication device associated with each of the multiple users being at least one of an electronic health tracker or an electronic activity tracker. In some embodiments and situations, the described techniques include implementing and/or using a computer-implemented method comprising determining, by one or more computer devices, that an electronic communication device is within a geofence around a property at a time associated with a showing appointment scheduled for the property, the electronic communication device being associated with a user scheduled to participate in the showing appointment; performing, by the one or more computer devices and in response to the determining and before the showing appointment begins, a health check process for the user, including using the electronic communication device to determine one or more values for one or more health parameters for the user, and determining whether the one or more values satisfy one or more defined criteria; and controlling, by the one or more computer devices, access of the user to the property for the showing appointment based on the performing of the health check process, including providing, only if the one or more values are determined to satisfy the one or more defined criteria, a showing directive to enable the showing appointment to occur. Such a computer-implemented method may further involve one or more of the following: the showing directive including at least one of a showing pass or a key code corresponding to the showing appointment; and/or the performing of the health check process for the user including presenting one or more health inquiries to the user via the electronic communication device, and determining whether one or more responses to the one or more health inquiries obtained via the electronic communication device meets a set of health requirements; and/or the one or more computer devices including one or more server computer devices, with the determining and the performing and the controlling including exchanging electronic communications between the one or more server computer devices and the electronic communication device; and/or the one or more computer devices including the electronic communication device; and/or the one or more health parameters include at least one of heart rate, or heart rate variability, or blood pressure, or respiratory rate, or walking pace, or distance traveled, or blood oxygen level, or blood glucose level, or calories expended, or sleep characteristics; and/or the electronic communication device being at least one of a smart watch, or an electronic health tracker, or an electronic activity tracker, or a pacemaker, or an implantable electronic heart device; and/or the one or more health parameters including multiple of heart rate, or heart rate variability, or blood pressure, or respiratory rate, or walking pace, or distance traveled, or blood oxygen level, or blood glucose level, or calories expended, or sleep characteristics.

BRIEF DESCRIPTION OF THE DRAWINGS

Although characteristic features will be particularly pointed out in the claims, particular features may be better understood by referring to the following description taken in connection with the accompanying drawings forming a part hereof, wherein like reference numerals refer to like parts throughout the several views and in which:

A person of ordinary skills in the art will appreciate that elements of the figures above are illustrated for simplicity and clarity, and are not necessarily drawn to scale. The dimensions of some elements in the figures may have been exaggerated relative to other elements to help understanding of the present teachings. Furthermore, a particular order in which certain elements, parts, components, modules, steps, actions, events and/or processes are described or illustrated may not be actually required. A person of ordinary skills in the art will appreciate that, for the purpose of simplicity and clarity of illustration, some commonly known and well-understood elements that are useful and/or necessary in a commercially feasible embodiment may not be depicted in order to provide a clear view of various embodiments in accordance with the present teachings.

DETAILED DESCRIPTION

Figure 1:
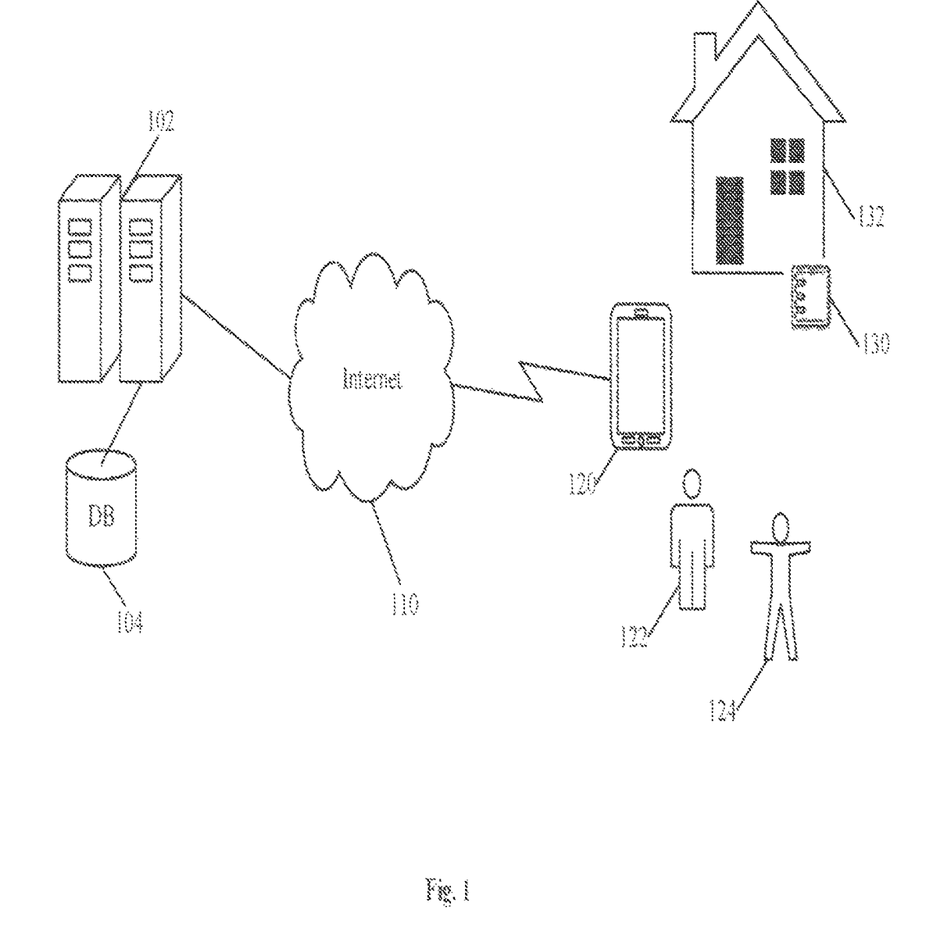
FIG. 1 is an illustrative block diagram of a real estate showing system in accordance with the teachings of this disclosure.

The present disclosure provides automated techniques for controlling access of users to physical properties based at least in part on health parameters of the users, including performing automated activities involving assessing and using body temperature and/or other health parameters of the users. Turning to the Figures and to FIG. 1 in particular, some or all of the automated techniques are implemented in at least some embodiments by a real estate showing system as generally indicated at 100. The real estate showing system 100 is adapted to perform processes in accordance with the present teachings to manage showing appointments based on one or more health parameters of showing contacts. In one illustrative embodiment, the real estate showing system 100 includes a real estate showing appointment management server system 102, which comprises one or more servers (such as a cloud server system, a server farm or a set of individual servers), and one or more databases 104 for storing listing contacts, listings, showing appointments, showing media, showing data, etc. The databases 104 (such as a cloud database system, a relational database system, an in-memory database, etc.) are operatively coupled to the servers 102 via, for example, networking links.

The real estate showing system 100 further includes electronic communication computer devices, one of which is illustrated and indicated at 120, communicating with the server system 102 via the Internet 110. The device 120 can be and/or be associated with a smartphone, a tablet computer (such as an iPad), a laptop computer, a smart watch, an electronic health tracker, an electronic activity tracker, a pacemaker or other implantable electronic heart device (e.g., implantable cardioverter-defibrillator), or other types of mobile devices, and may be configured to measure and/or predict values for various types of health parameters of a user who wears and/or carries the device (e.g., body temperature, heart rate, heart rate variability, blood pressure, respiratory rate, walking pace or other measure of distance traveled, blood oxygen level, blood sugar or glucose level, calories expended, sleep time and/or other sleep characteristics, etc.). The devices are operated by showing contacts, such as a showing agent 122.

The server system 102 runs a specialized server software application for managing listings, scheduling showings and managing showing appointments. The specialized server software application is physically loaded in a single server or distributed across multiple servers within the server system 102. The specialized server software application includes one or more computer software programs coded using computer programming languages, such as Java, C#, etc. Moreover, the showing management system 102 integrates with or connects to one or more listing services (not shown) to update the database 104 of real estate property listings and other real estate related data.

Figure 2:
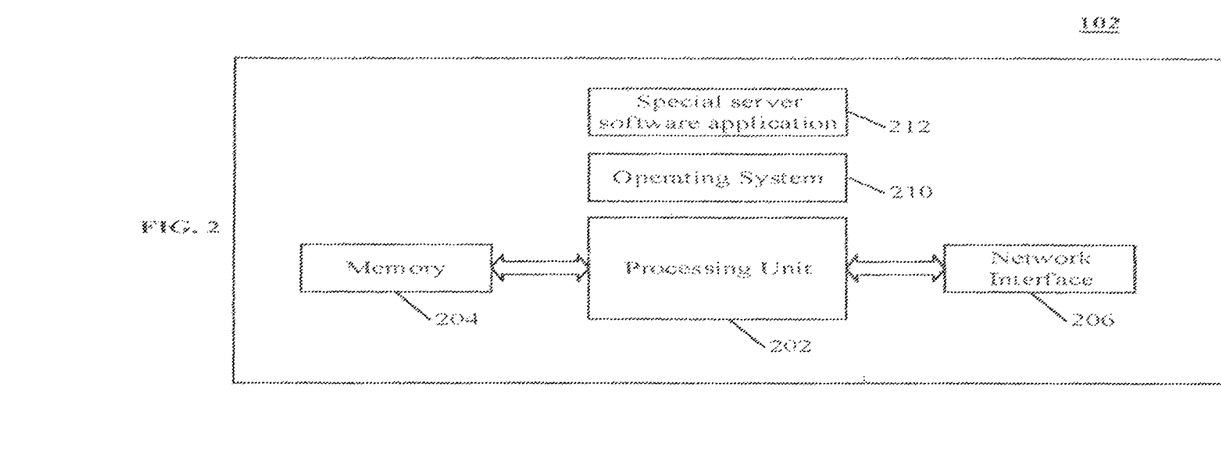
FIG. 2 is an illustrative block diagram of a real estate showing appointment management server system in accordance with the teachings of this disclosure.

In accordance with the present teachings, as shown in FIG. 2, each server 102 includes a server processing unit 202, one or more server network interfaces 206 through which the server system 102 accesses the Internet 102 and communicates with the database 104, and some amount of server memory 204. The network interface 206 and the memory 204 are operatively coupled to the processing unit 202. An operating system (such as Windows and Linux) 210 runs on the processing unit 202. The server system 102 further includes the special server software application indicated at 212 executed by the processing unit 202 for managing listings, and showing appointments.

Each of the electronic communication devices 120 includes a processing unit, an audio output interface (such as a speaker), an audio input interface (such as a microphone), a user input interface (such as a touch screen), some amount of memory, a video output interface (such as a display screen), a video input interface (such as a camera), and a network interface. The elements of the device 120 are operatively coupled to its processing unit. The electronic communication device 120 further includes a special computer software application executed by its processing unit. The special computer software application includes one or more computer software programs coded using computer programming languages, and is also referred to herein as a mobile app.

The showing agent 122 operates the device 120 and visits the real estate property 132 for showing the same for her/his client user 124. The user 124 can be, for example, a prospect buyer, a prospect tenant, or a professional for accessing the property 132 (e.g., an inspector, appraiser, repair person, etc.). The property 132 is represented as a listing inside the showing system 102. The special computer software application running on the device 120 communicates with the server system 102 for managing the showing, including to control access of the user to the property based on determining that one or more values for one or more health parameters for the user satisfy one or more defined criteria, such as by providing, only if the one or more values are determined to satisfy the one or more defined criteria, a showing directive to enable the showing appointment to occur. The showing directive may, for example, correspond to a listing physical access control device 130 that enables physical access to the property 132 for the listing, such as an electronic or non-electronic lockbox, an electronic smart lock or other electronic lock, etc. The access control device 130 allows or disallows the showing agent 122 to get into the property 132, and thus the computer software application controls access to the property for the showing via the providing (or not providing) of such a showing directive.

Figure 3:
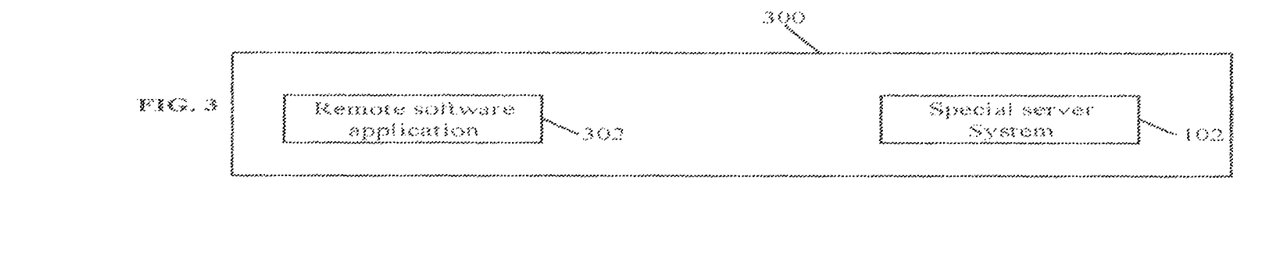
FIG. 3 is an illustrative block diagram of a real estate showing appointment management system in accordance with the teachings of this disclosure.
Figure 4:
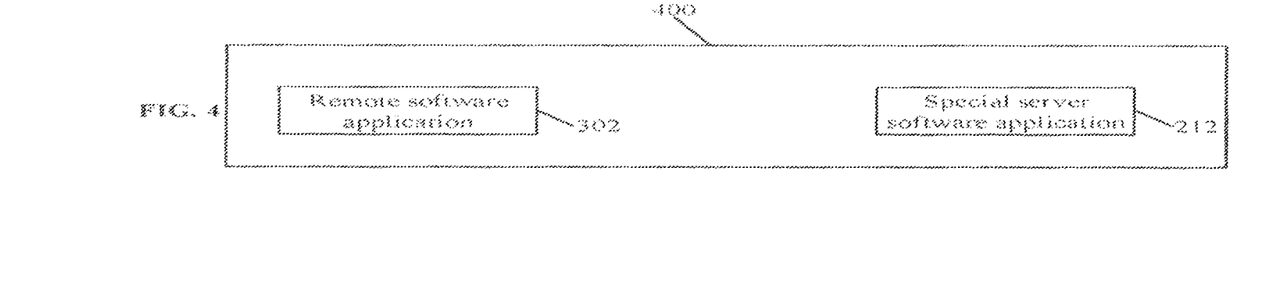
FIG. 4 is an illustrative block diagram of a real estate showing appointment management software system in accordance with the teachings of this disclosure.

Referring to FIGS. 3 and 4, the special computer software application is indicated at 302. The server system 102 with the specialized server software application 212 and the software application 302 are collectively referred to herein as the real estate showing appointment management system, indicated at 300. The specialized server software application 212 and the software application 302 are collectively referred to herein as the real estate showing appointment management software system, indicated at 400. The real estate showing appointment management software system 400 is a subsystem of the real estate showing appointment management system 300.

The real estate showing agent 122 operates a computer device (e.g., the device 120) to access the showing appointment management system 300 to schedule showing appointments for showing real estate properties (also referred to herein as listings), provide showing feedback, and retrieve showing appointments. The showing appointment can be encoded into a showing pass, such as a machine readable optical label or barcode. A listing contact (such as a listing agent and the seller of a listing) can also use a computer device to access the showing appointment management system 300 to manage listings, confirm showing appointments, and retrieve showing feedback. Such features can also be performed by mobile computer devices, such as smartphones, tablet computers, etc.

Figure 5:
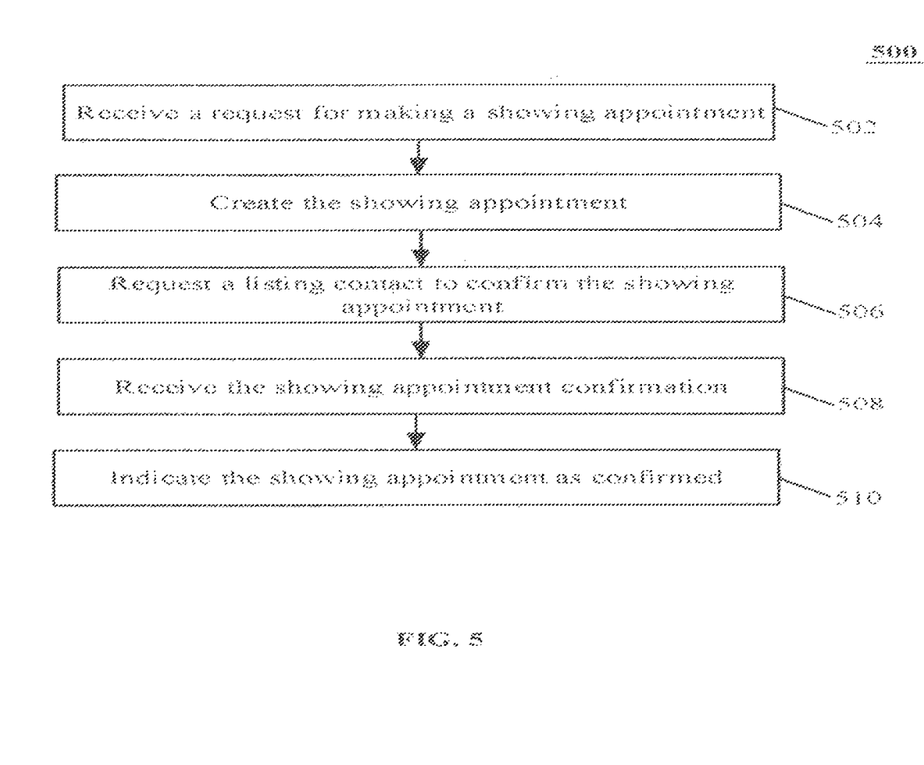
FIG. 5 is a flowchart illustrating a process by which a real estate showing appointment management system creates showing appointments in accordance with the teachings of this disclosure.

Referring now to FIG. 5, a flowchart depicting a process by which the showing appointment management system 300 creates showing appointments is shown and generally indicated at 500. At 502, the server software application 212 receives a request for making a showing appointment to show a particular listing, such as the listing 132. The showing appointment request can be made by the showing agent 120 through the device 122 or a different computer device. At 504, the server software application 212 creates the showing appointment, and stores it into the database 104. At 506, the server software application 212 sends a request to a listing contact (such as the listing agent) to confirm the showing appointment. Once the listing contact confirms the showing appointment, at 508, the server software application 212 receives the confirmation. At 510, the server software application 212 indicates that the showing appointment has been confirmed. The indication can be done by modifying database records stored in the database 104. At this point, the showing appointment has been successfully scheduled.

Figure 6A:
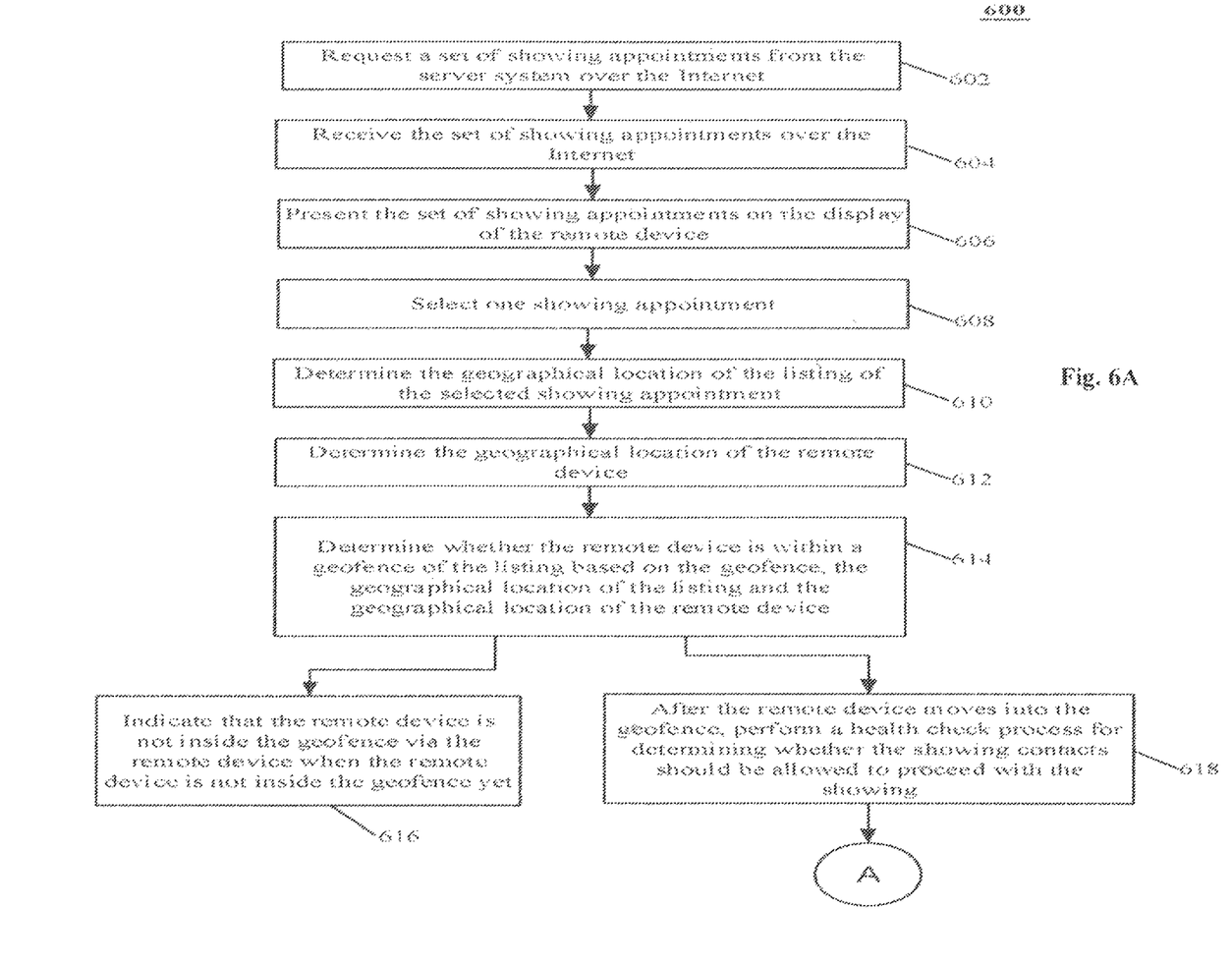
FIGS. 6A and 6B are a flowchart illustrating a process by which a real estate showing appointment management system manages showing appointments based on a set of health parameters in accordance with the teachings of this disclosure.
Figure 6B:
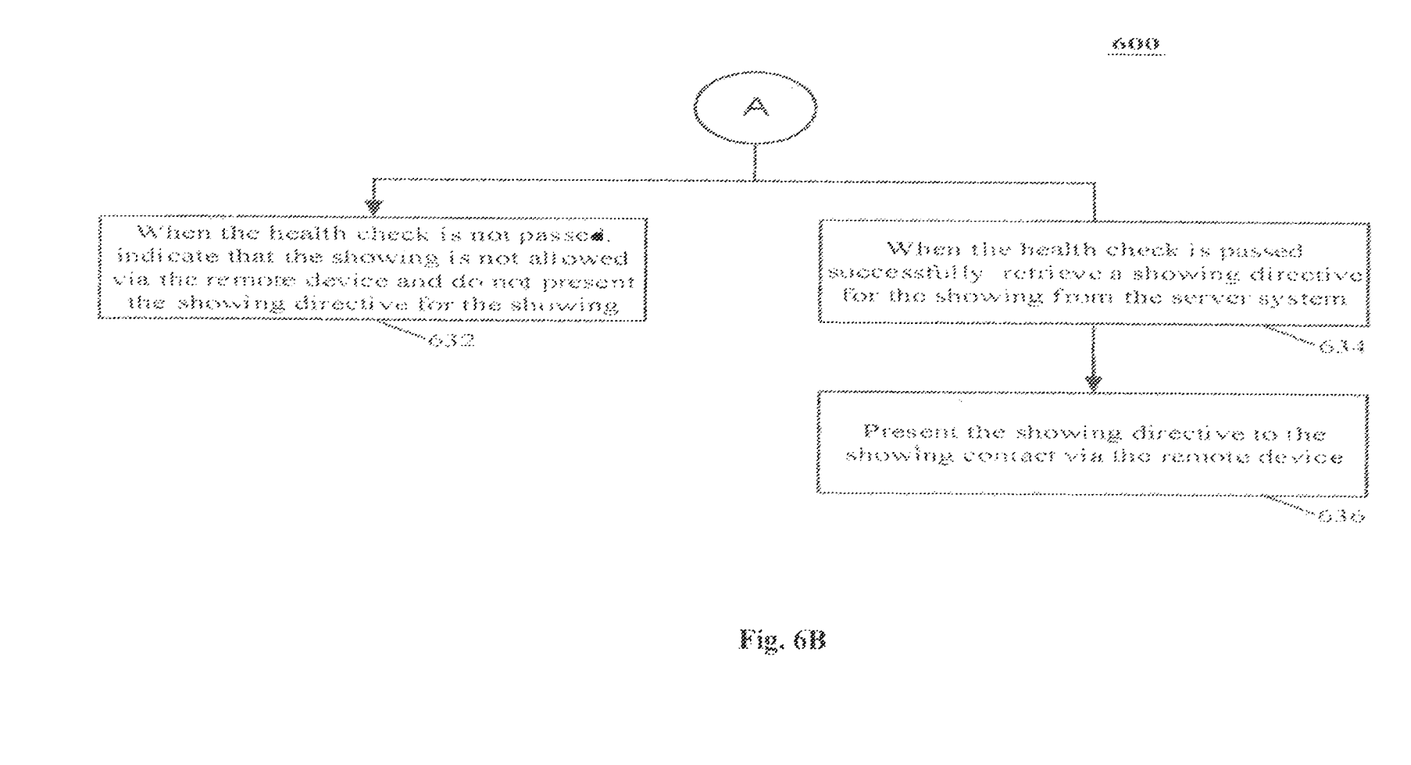

Referring now to FIGS. 6A and 6B, a flowchart depicting a process by which the showing appointment management system 300 manages showing appointments based on health parameters is shown and generally indicated at 600. At 602, the special computer software application 302 sends to the special server software application 212 a request for showing appointments of the showing agent 122 over the Internet 110. For example, when the software application 302 requests all showing appointments of the showing agent 122 of a particular day, within a particular amount of time from the current time, within a particular range of the current geographical location (i.e., GPS location) of the device 120, etc. Taking the particular day scenario as an example, the software application 302 may request all showing appointments of the showing agent 122 for the current day. As another example, the software application 302 sends the current GPS location of the device 120 to the server software application 212, and indicates a request for showing appointments of listings within a predetermined radius of the GPS location.

In response, the server software application 212 retrieves the set of showing appointments meeting the criteria of the request from the database 104, and sends the same to the device 120. At 604, the software application 302 receives the set of showing appointments. At 606, the software application 302 presents the set of showing appointments and/or the underlying listings on a display screen of the device 120. The showing agent 122 selects one of them via the input interface of the device 120. In response to the showing agent's 122 selection input, at 608, the software application 302 selects one showing appointment from the set. At 610, the software application 302 determines the geographical location of the listing of the selected showing appointment. In one implementation, the geographical location is provided as part of the showing appointment data received at 604. In a different implementation, it is requested from the server software application 212. For instance, it is part of the listing data of the listing that is provided to the software application 302 separate from the showing appointment data. In yet another different implementation, the geographical location is not provided to the device 120. In such a case, at 610, the software application 302 determines that the geographical location is only available to the server software application 212.

At 612, the software application 302 determines the geographical location (i.e., GPS location) of the device 120. The element 612 may be performed periodically. At 614, based on a geofence of the listing 132 and the GPS locations of the listing 132 and the device 120, the software application 302 determines whether the device 120 is within the geofence of the listing 132. The geofence defines a range around the listing 132. The range can be defined by a radius, such as fifty meters, or a rectangular or square area around the listing 132. In one implementation, the geofence is provided as part of the showing appointment data received at 604. In a different implementation, it is requested from the server software application 212. For instance, it is part of the listing data of the listing 132 that is provided to the software application 302 separate from the showing appointment data received at 604.

As used herein, the GPS location of the device 120 is deemed to be that of the showing agent 122. When the device 120 is not inside the geofence, at 616, the software application 302 indicates that the showing agent 122 is not at the listing 132 yet. The indication can be, for example, a message displayed on the screen of, a video message played by, or an audio message played back by the device 120.

When the device 120 moves into the geofence, the software application 302 interprets that the showing agent 122 is at the listing 132 now. In such a case, at 618, the software application 302 performs a health check on the showing contacts 122-124 to determine whether they should be allowed to proceed with the showing. If allowed, the showing agent 122 can then proceed with the showing appointment, access the listing 132 and show it to the prospect buyer 124. When showing contacts 122-124 fail the health check (meaning that the health check is not passed), at 632, the software application 302 indicates that the showing contacts 122-124 are not allowed to access the listing 132 since one of them has failed the heath check. The indication can be, for example, a message displayed on the screen of, a video message played by, or an audio message played back by the device 120.

When the showing contacts 122-124 fail the health check (meaning that the health check is not passed), at 632, the software application 302 indicates that the showing contacts 122-124 are not allowed to access the listing 132 since one of them has failed the heath check. The indication can be, for example, a message displayed on the screen of, a video message played by, or an audio message played back by the device 120. When the showing contacts 122-124 pass the health check (meaning that the health check is passed), at 634, the software application 302 retrieves a showing directive for the selected showing appointment. The showing directive allows the showing agent 122 to move forward with the showing of the listing 132. Without the showing directive, the showing contact 122 cannot proceed with the showing.

In one implementation, the showing directive is provided at 604 as part of the showing appointment data. Alternatively, the showing directive is separately requested from the server software application 212 by the software application 302. The showing directive can be a showing pass. The showing pass is scanned by the listing access control device 130. Once the listing access control device 130 verifies the showing pass directly or indirectly, the listing 132 is opened for access by the showing agent 122 to show it for the prospect buyer 124. The showing directive can also be a different type of access credentials, such as a key code or other access code, to open the listing access control device 130. It is displayed on the screen of or played back as an audio message by the device 120. Moreover, the showing directive can include one or more showing instructions. The showing instructions are configured by the listing agent and/or the owner of the property 132. They direct the showing contacts 122-124 to do and/or not to do certain things during the showing of the house 132.

Figure 7:
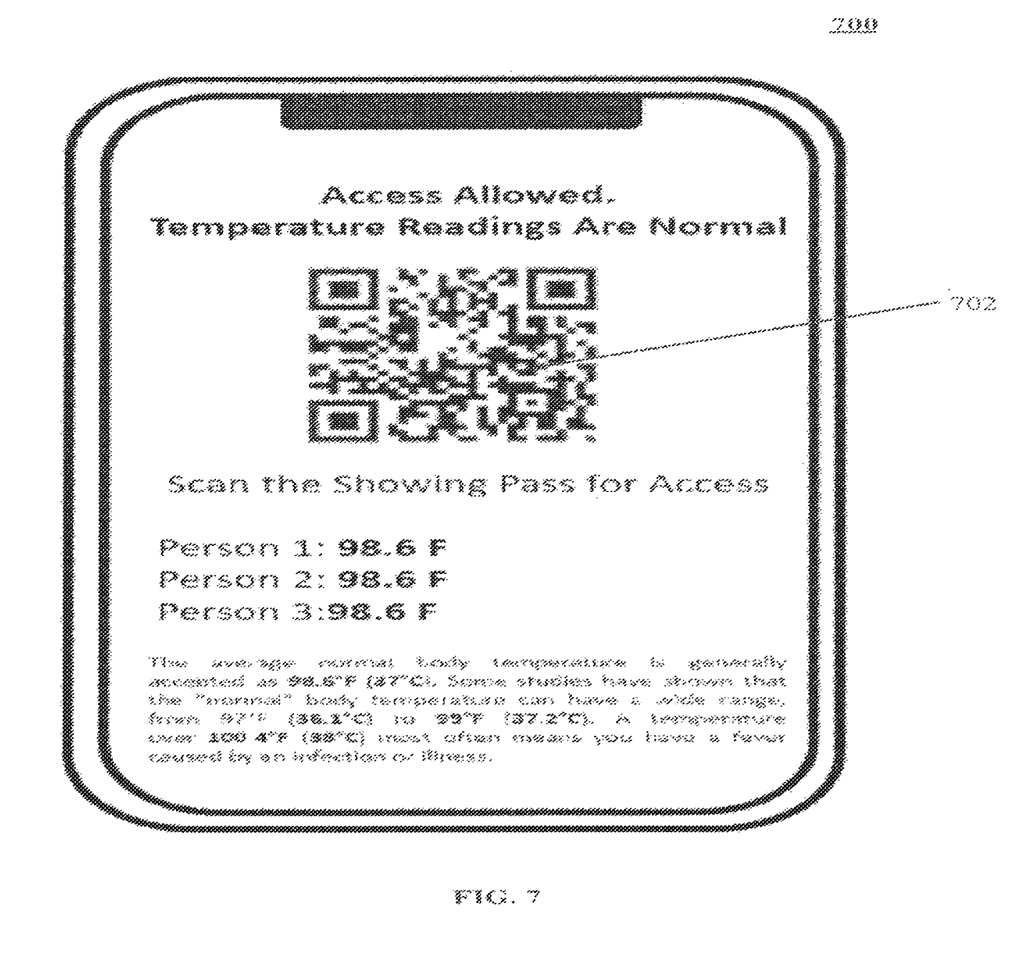
FIG. 7 is an illustrative screenshot of an electronic communication device showing a showing directive in accordance with the teachings of this disclosure.

At 636, the software application 302 presents the showing directive to the showing agent 122 by the device 120. An illustrative showing directive is shown in FIG. 7. Referring to FIG. 7, an illustrative screenshot of the device 120 showing a showing directive 702 is shown and generally indicated at 700. The illustrative showing directive 702 is a showing pass.

Figure 8:
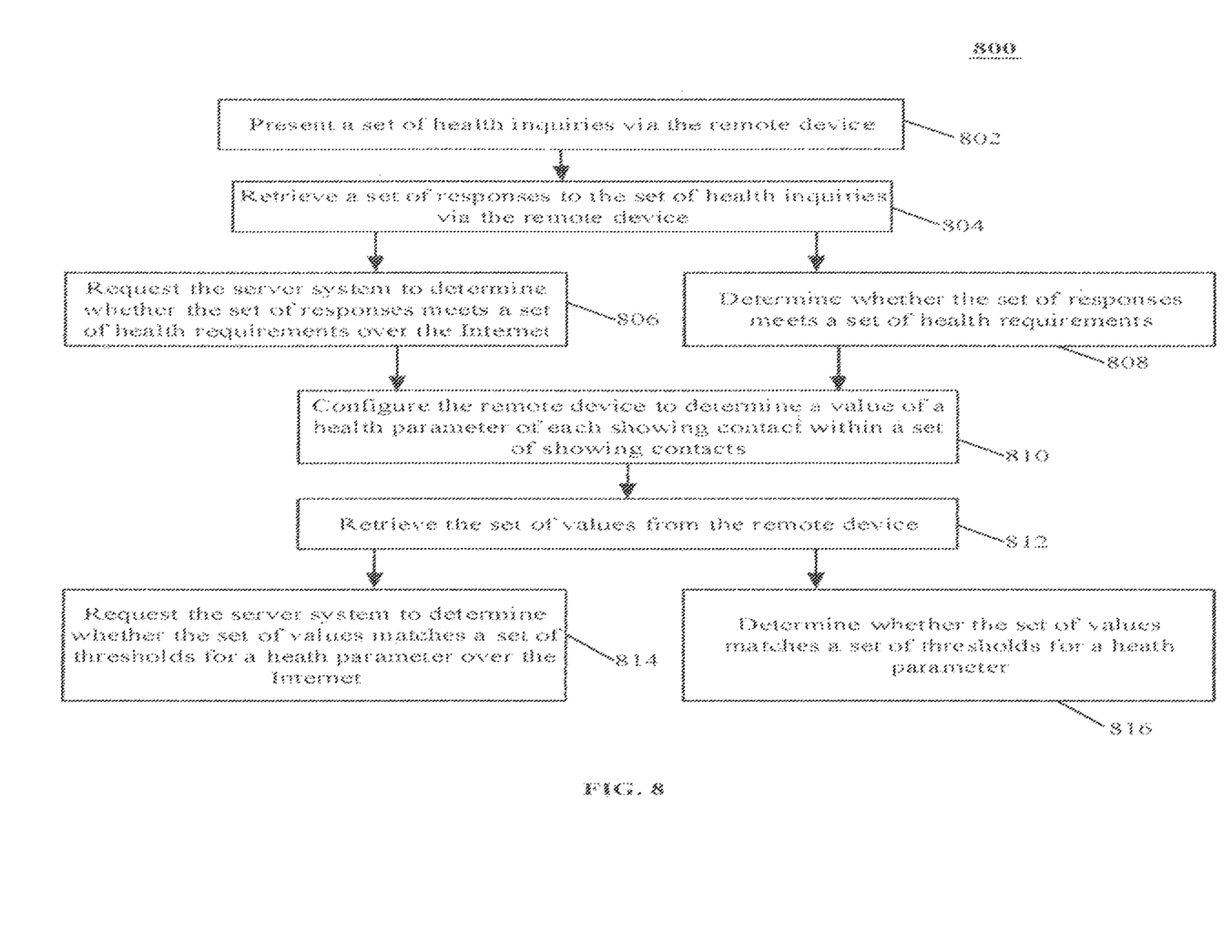
FIG. 8 is a flowchart illustrating a process by which a computer software application performs a health check on a set of showing contacts in accordance with the teachings of this disclosure.

The health checking process performed at 618 is further illustrated by reference to FIGS. 8, 9 and 10. Turning first to FIG. 8, a flowchart illustrating a process by which the computer software application 302 performs to check a set of health parameters of the showing contacts 122-124 is shown and generally indicated at 800. At 802, the software application 302 presents a set of one or more health inquiries to a user via the device 120, with one or more responses to the health inquiries serving as one or more health parameter values for the user. The presentation may take, for example, the form of audio, text, graphical and/or video, with an illustrative presentation of the health inquiries shown in FIG. 9. Such health inquiries to a user may include, for example, one or more of the following: one or more questions about a past and/or current infection of the user and/or of one or more other associated users (e.g., other members of a group that includes the user); one or more questions about past and/or current activities of the user and/or of one or more other associated users, such as that may affect health of the user(s) (e.g., taking medications, being around others who are infected or otherwise sick, traveling to an area associated with people who are infected or otherwise sick, receiving vaccinations, having previous infections or sicknesses that may impart current protection against sickness, etc.); one or more questions about past and/or current conditions of the user and/or of one or more other associated users, such as that may affect health of the user(s); one or more questions about a past and/or current value for a health parameter of the user and/or of one or more other associated users (e.g., as obtained by the user from an associated device that is not in electronic communication with the device 120); one or more questions about a physical response of the user and/or of one or more other associated users to an indicated activity; one or more questions about a past and/or current symptom of the user and/or of one or more other associated users; one or more questions about past and/or current demographic information of the user and/or of one or more other associated users, such as that may affect health of the user(s); etc.

Figure 9:
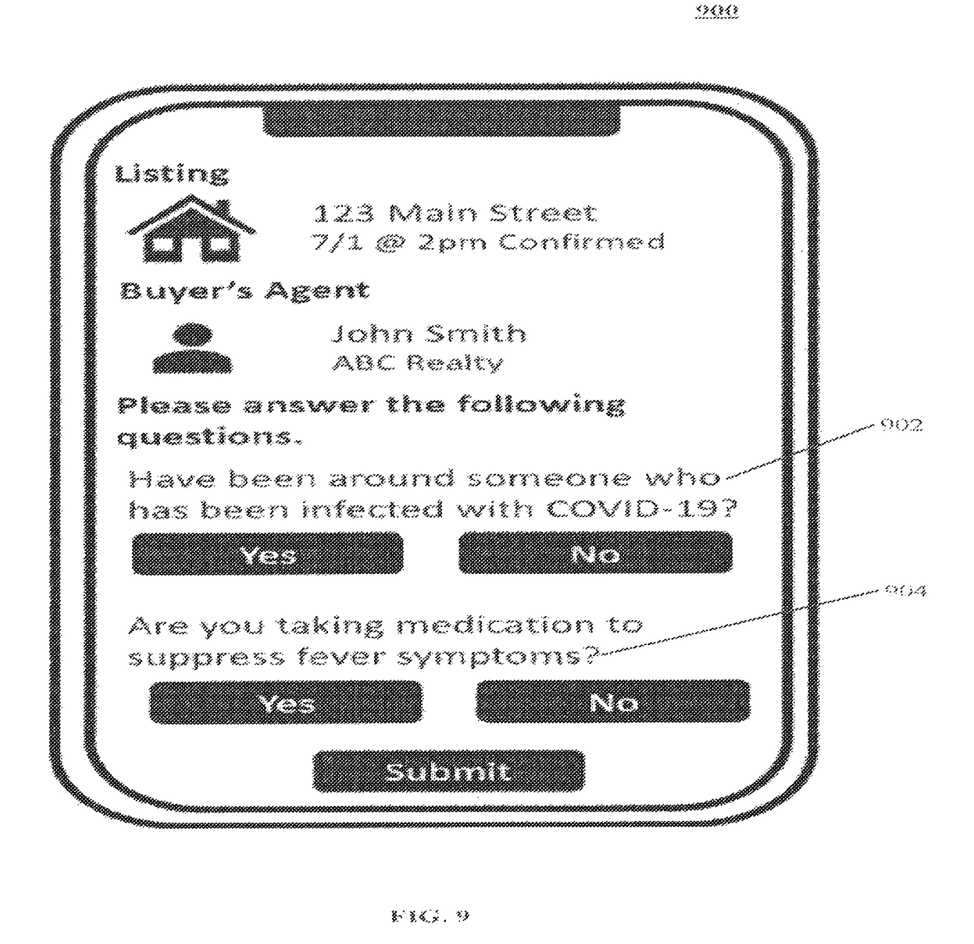
FIG. 9 is an illustrative screenshot of a set of health inquiries for a real estate showing appointment presented by a computer software application on an electronic communication device in accordance with the teachings of this disclosure.

Referring to FIG. 9 now, an illustrative screenshot of the set of health inquiries 902 and 904 is shown and generally indicated at 900. Via the screen 900, the showing agent 122 enters her/his responses, and then submits the responses.

Turning back to FIG. 8, at 804, the software application 302 retrieves the responses entered by the showing agent 122. In one implementation, at 806, the software application 302 submits the set of responses to the server software application 212 and requests it to determine whether the set of responses meets a set of health requirements. For example, for the showing agent 122 to proceed with the showing, the response to the inquiry 902 needs to be No. The software application 302 is said to determine whether the set of responses meets the set of health requirements relying on the server software application 212.

Alternatively, the server software application 212 provides the set of health requirements to the software application 302. In such a case, at 808, the software application 302 compares the set of responses to the set of health requirements to determine whether the set of responses meets the set of health requirements. In such a case, software application 302 is said to determine whether the set of responses meets the set of health requirements by itself.

At 810, the software application 302 configures the device 120 to determine the value of a health parameter of each showing contact within the set of showing contacts 122-124. In one embodiment, the health parameter is the human body temperature. The electronic device 120, such as a smartphone, is capable of obtaining the body temperature of the showing agents 122-124. For instance, the device 120 is capable to detect the human body temperature by incorporating an infrared thermometer. At 810, the software application 302 activates and/or accesses the infrared thermometer via, for example, an application programming interface ("API") call. In one implementation, right before or after the element 808, the software application 302 instructs the showing agent 122 to take certain steps, such as placing the top-rear end of the device 120 against or near her/his forehead for taking her/his body temperature. The instruction may also include what actions, such as pressing a button, the showing agent 122 should take for taking her/his body temperature. More than one health parameter can be operated on at 810.

At 812, the software application 302 retrieves the body temperature of the showing contact. For instance, the temperature is returned via a call back to the software application 302, or another AP! call to request the temperature. The body temperature retrieved at 812 is a value of the body temperature health parameter. The body temperature is taken of each showing contact. At 814, the software application 302 submits the set of values to the server system 102, and requests the server software application 212 to determine whether the set of values matches a set of thresholds. For instance, with the normal human body temperature range being 97°-990, the threshold can be 99°. If any value within the set is above 99°, it is said herein that the set of values does not match the threshold and the showing contacts 122-124 have faded the health check. On the other side, if all values within the set are not above 99°, it is said that the set of values does match the threshold and the showing contacts 122-124 have passed the health check. When the software application 302 requests the server software application 212 to determine whether the set of values matches a set of thresholds, it is also said that the software application 302 determines whether the set of values matches a set of thresholds relying on the server software application 212.

In a different implementation, at 816, the software application 302 determines whether the set of values matches a set of thresholds. In such a case, the software application 302 retrieves the set of health thresholds from the server software application 302. The set of health thresholds can be retrieved at 604. Alternatively, it is retrieved via a separate request to the server system 102. After 814 and 816, the software application 302 performs the element 634. In such a case, it is said that the software application 302 determines whether the set of values matches a set of thresholds by itself.

Figure 10:
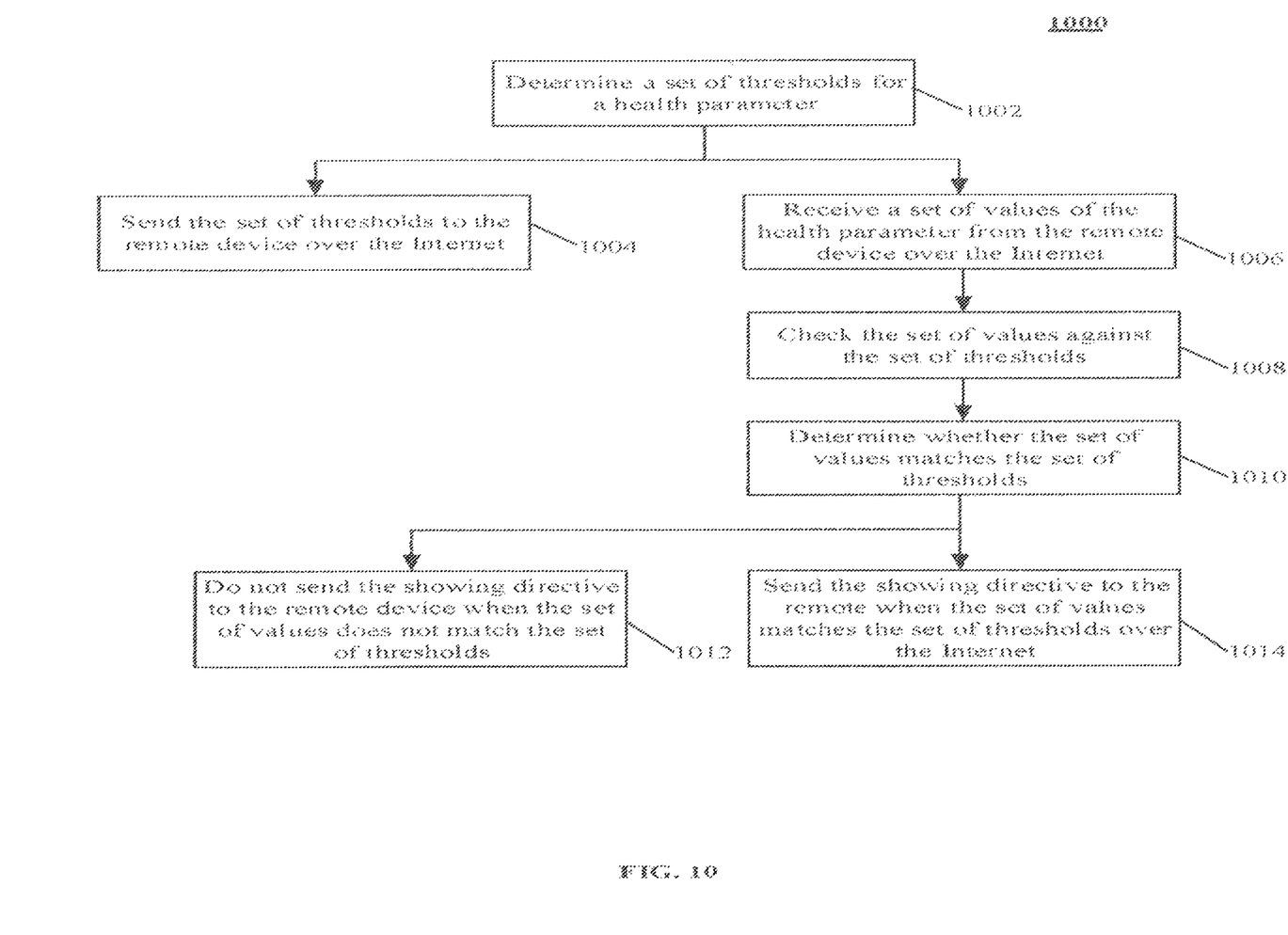
FIG. 10 is a flowchart illustrating a process by which a special real estate showing appointment management server software application manages showing appointments based on a health parameter in accordance with the teachings of this disclosure.

Referring to FIG. 10, a flowchart depicting a process by which the special server software application 212 manages showing appointments based on a health parameter is shown and generally indicated at 1000. At 1002, the server software application 212 determines the set of thresholds for a health parameter, such as that referenced at 800. The set of thresholds can be enabled and/or configured by the listing agents, homeowners, the provider of the system 300, etc., and stored in the database 104. At 1004, the server software application 212 sends the set of thresholds to the software application 302. For instance, it is sent along with the showing appointment data. Alternatively, it is sent in response to a request from the software application 302.

Alternatively, the server software application 212 does not send the set of health thresholds to the device 120. In such a case, at 1006, the server software application 212 receives the set of values sent at 814. At 1008, the server software application 212 compares the set of values against the set of thresholds. At 1010, the server software application 212 determines whether the set of values matches the set of thresholds. When the set of values does not match the set of thresholds, at 1012, the server software application 212 does not send the showing directive to the device 120, such that the showing agent 122 cannot proceed with the showing of the listing 132. On the other side, when the set of values does match the set of thresholds, at 1014, the server software application 212 sends the showing directive to the device 120, such that the showing agent 122 can proceed with the showing of the listing 132.

Obviously, many additional modifications and variations of the present disclosure are possible in light of the above teachings. Thus, it is to be understood that, within the scope of the appended claims, the disclosure may be practiced otherwise than is specifically described above.

The foregoing description of the disclosure has been presented for purposes of illustration and description, and is not intended to be exhaustive or to limit the disclosure to the precise form disclosed. The description was selected to best explain the principles of the present teachings and practical application of these principles to enable others skilled in the art to best utilize the disclosure in various embodiments and various modifications as are suited to the particular use contemplated. It is intended that the scope of the disclosure not be limited by the specification, but be defined by the claims set forth below. In addition, although narrow claims may be presented below, it should be recognized that the scope of this disclosure is much broader than presented by such claim(s). It is intended that broader claims will be submitted in one or more applications that claim the benefit of priority from this application. Insofar as the description above and the accompanying drawings disclose additional subject matter that is not within the scope of the claim or claims below, the additional disclosures are not dedicated to the public and the right to file one or more applications to claim such additional disclosures is reserved.

What is claimed is:

1. A real estate showing appointment management system comprising:
    one or more processors; and
    one or more memories with stored software that, when executed by the one or more processors, causes the one or more processors to perform operations including at least:
        obtaining information about a showing appointment scheduled for a property during a time period, including multiple users that are scheduled to participate in the showing appointment and that each has a respective associated electronic communication device;
        establishing a geofence around the property before the time period; and
        controlling access of the multiple users to the property for the showing appointment, including, for each of the multiple users,
            determining that the electronic communication device associated with the user is within the geofence;
            performing, in response to the determining and before the showing appointment begins, a health check process for the user, including using the electronic communication device associated with the user to determine one or more values for one or more health parameters for the user, and determining whether the one or more values satisfy one or more defined criteria; and
            presenting, on the electronic communication device associated with the user, a showing directive to enable the showing appointment to occur only if the one or more values for the one or more health parameters for the user are determined to satisfy the one or more defined criteria.

2. The real estate showing appointment management system of claim 1 wherein the showing directive includes at least one of a showing pass or a key code corresponding to the showing appointment.

3. The real estate showing appointment management system of claim 1 wherein the performing of the health check process for a user includes:
    presenting a set of health inquiries to the user via the electronic communication device associated with the user; and
    determining whether a set of responses to the set of health inquiries obtained via the electronic communication device meets a set of health requirements.

4. The real estate showing appointment management system of claim 1 wherein the one or more processors and the one or memories are part of one or more server computer devices, and wherein the operations include exchanging electronic communications between the one or more server computer devices and the electronic communication devices associated with the multiple users.

5. The real estate showing appointment management system of claim 1 further comprising the electronic communication devices associated with the multiple users and include multiple processors and multiple memories, wherein the one or more processors include at least the multiple processors, and wherein the one or memories include at least the multiple memories.

6. The real estate showing appointment management system of claim 1 wherein the one or more health parameters include at least one of heart rate, or heart rate variability, or blood pressure, or respiratory rate, or walking pace, or distance traveled, or blood oxygen level, or blood glucose level, or calories expended, or sleep characteristics.

7. The real estate showing appointment management system of claim 1 wherein the one or more health parameters include two or more of heart rate, or heart rate variability, or blood pressure, or respiratory rate, or walking pace, or distance traveled, or blood oxygen level, or blood glucose level, or calories expended, or sleep characteristics.

8. The real estate showing appointment management system of claim 1 wherein the electronic communication device associated with one of the multiple users includes at least one of a smart watch, or an electronic health tracker, or an electronic activity tracker, or a pacemaker, or an implantable electronic heart device.

9. The real estate showing appointment management system of claim 1 wherein, for each of the multiple users, the electronic communication device associated with the user is at least one of an electronic health tracker or an electronic activity tracker.

10. A computer-implemented method comprising:
    determining, by one or more computer devices, that an electronic communication device is within a geofence around a property at a time associated with a showing appointment scheduled for the property, the electronic communication device being associated with a user scheduled to participate in the showing appointment;
    performing, by the one or more computer devices and in response to the determining and before the showing appointment begins, a health check process for the user, including using the electronic communication device to determine one or more values for one or more health parameters for the user, and determining whether the one or more values satisfy one or more defined criteria; and
    controlling, by the one or more computer devices, access of the user to the property for the showing appointment based on the performing of the health check process, including providing, only if the one or more values are determined to satisfy the one or more defined criteria, a showing directive to enable the showing appointment to occur.

11. The computer-implemented method of claim 10 wherein the showing directive includes at least one of a showing pass or a key code corresponding to the showing appointment.

12. The computer-implemented method of claim 10 wherein the performing of the health check process for the user includes:
    presenting one or more health inquiries to the user via the electronic communication device; and determining whether one or more responses to the one or more health inquiries obtained via the electronic communication device meets one or more health requirements.

13. The computer-implemented method of claim 10 wherein the one or more computer devices include one or more server computer devices, and wherein the determining and the performing and the controlling include exchanging electronic communications between the one or more server computer devices and the electronic communication device.

14. The computer-implemented method of claim 10 wherein the one or memories computer devices include the electronic communication device.

15. The computer-implemented method of claim 10 wherein the one or more health parameters include at least one of heart rate, or heart rate variability, or blood pressure, or respiratory rate, or walking pace, or distance traveled, or blood oxygen level, or blood glucose level, or calories expended, or sleep characteristics.

16. The computer-implemented method of claim 15 wherein the electronic communication device is at least one of a smart watch, or an electronic health tracker, or an electronic activity tracker, or a pacemaker, or an implantable electronic heart device.

17. The compute implemented method of claim 10 wherein the one or more health parameters include multiple of heart rate, or heart rate variability, or blood pressure, or respiratory rate, or walking pace, or distance traveled, or blood oxygen level, or blood glucose level, or calories expended, or sleep characteristics.

18. The computer-implemented method of claim 17 wherein the electronic communication device is an electronic health tracker or an electronic activity tracker.

19. The computer-implemented method of claim 10 wherein the electronic communication device includes at least one of a smart watch, or an electronic health tracker, or an electronic activity tracker, or a pacemaker, or an implantable electronic heart device.

20. The computer-implemented method of claim 10 wherein the electronic communication device is an electronic health tracker or an electronic activity tracker.

* * * * *

UNITED STATES PATENT AND TRADEMARK OFFICE
CERTIFICATE OF CORRECTION

PATENT NO. : 12,125,590 B2
APPLICATION NO. : 17/890151
DATED : October 22, 2024
INVENTOR(S) : Michael P. Caputo et al.

It is certified that error appears in the above-identified patent and that said Letters Patent is hereby corrected as shown below:

In the Claims

Column 14, Line 9, Claim 5:
"processors, and wherein the one or memories include at least" should read --processors, and wherein the one or more memories include at least--.

Column 15, Line 12, Claim 14:
"wherein the one or memories computer devices include the" should read --wherein the one or more computer devices include the--.

Column 16, Line 4, Claim 17:
"17. The compute implemented method of claim 10" should read --17. The computer-implemented method of claim 10--.

Signed and Sealed this
Nineteenth Day of November, 2024

Katherine Kelly Vidal
*Director of the United States Patent and Trademark Office*